United States Patent [19]

Mohacsi

[11] Patent Number: 5,225,557

[45] Date of Patent: Jul. 6, 1993

[54] PROCESS FOR MAKING OPTICALLY ACTIVE NAPHTHO[1,2-B]THIAZEPIN-4(5H)-ONES

[75] Inventor: Erno Mohacsi, Summit, N.J.

[73] Assignee: Hoffmann-La Roche Inc., Nutley, N.J.

[21] Appl. No.: 624,832

[22] Filed: Dec. 10, 1990

Related U.S. Application Data

[62] Division of Ser. No. 373,741, Jun. 29, 1989, Pat. No. 4,996,325, which is a division of Ser. No. 192,252, May 10, 1988, Pat. No. 4,864,058.

[51] Int. Cl.$^5$ .............................................. C07D 217/00
[52] U.S. Cl. .................................. 546/149; 540/495; 562/431; 562/433
[58] Field of Search ............... 540/495; 514/211; 562/431, 433; 546/149

[56] References Cited

U.S. PATENT DOCUMENTS 4,652,561  3/1987  Mohacsi et al. ............... 514/211

FOREIGN PATENT DOCUMENTS

| | | |
|---|---|---|
| 3337-176A | 4/1984 | Fed. Rep. of Germany . |
| 59-110668 | 6/1984 | Japan . |
| 59-144750 | 8/1984 | Japan . |
| 59-144751 | 8/1984 | Japan . |
| 60-243062 | 12/1985 | Japan . |
| 61-069756A | 4/1986 | Japan . |
| 8500250A | 1/1985 | Spain . |

*Primary Examiner*—John M. Ford
*Assistant Examiner*—Y. N. Gupta
*Attorney, Agent, or Firm*—George M. Gould; George W. Johnston; Ellen Ciambrone Coletti

[57] ABSTRACT

A process for preparing optically active naphtho[1.2-b][1,4]thiazepin-4(5H)-ones comprising resolution of rac-β-[(2-amino-1-naphthalenyl)thio]-α-hydroxy-4-methoxybenzenepropanoic acid and converting the optically active acids so obtained into final products is described. The end product naphtho[1,2-b][1,4]thiazepin-4(5H)-ones have activity as calcium channel blockers and accordingly are useful as agents for lowering blood pressure, and as agents for treating ischemia.

2 Claims, No Drawings

PROCESS FOR MAKING OPTICALLY ACTIVE NAPHTHO[1,2-B]THIAZEPIN-4(5H)-ONES

This is a division of application Ser. No. 07/373,741, filed Jun. 29, 1989, now U.S. Pat. No. 4,996,325, which is a division of application Ser. No. 07/192,252, filed May 10, 1988 now U.S. Pat. No. 4,864,058.

BRIEF SUMMARY OF THE INVENTION

The invention relates to a process for the preparation of optically active naphtho[1,2-b][1,4]thiazepin-4(5H)-ones which comprises resolving the racemic acid, rac-β-[(2-amino-1-naphthalenyl)thio]-α-hydroxy-4-methoxybenzenepropanoic acid of the formula

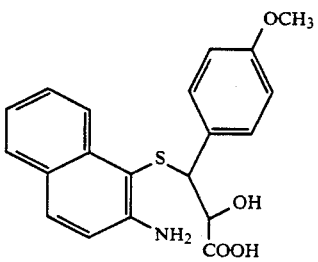

into its enantiomers and using said optically pure enantiomers for conversion into optically active naphtho[1,2-b][1,4]thiazepin-4(5H)-ones.

More specifically, the process of the invention comprises:

(a) treatment of a solution of the racemic acid, rac-β-[(2-amino-1-naphthalenyl)thio]-α-hydroxy-4-methoxybenzenepropanoic acid with (+)-1-(p-hydroxybenzyl)-1,2,3,4,5,6,7,8-octahydroisoquinoline to form diastereomeric salts (+)-β-[(2-amino-1-naphthalenyl) thio]-α-hydroxy-4-methoxybenzenepropanoic acid (+)-1-(p-hydroxybenzyl)-1,2,3,4,5,6,7,8-octahydroisoquinoline hydrate which crystallizes and (−)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate, which remains in solution;

(b) separating the crystalline diastereomeric salt of step (a) by filtration, and purifying by recrystallization;

(c) obtaining the optically pure enantiomeric acid (+)-β-[(2-amino-1-naphthalenyl)thio]-α-hydroxy-4-methoxybenzenepropanoic acid by treatment of the optically pure salt from step (b) with an inorganic acid;

(d) recovering the resolving agent (+)-1-(p-hydroxybenzyl)-1,2,3,4,5,6,7,8-octahydroisoquinoline;

(e) concentrating the mother liquor from step (b) and treating the residue with an inorganic acid; and isolating crude (−)-β-[(2-amino-1-naphthalenyl)thio]-β-hydroxy-4-methoxybenzenepropanoic acid by extraction;

(f) treating the crude acid from step (e) with (−)-1-(p-hydroxybenzyl)-1,2,3,4,5,6,7,8-octahydroisoquinoline separating the resulting crystalline salt by filtration and further purifying by recrystallization;

(g) obtaining the optically pure enantiomeric acid (−)-β-[(2-amino-1-naphthalenyl)thio]-α-hydroxy-4-methoxybenzenepropanoic acid by treating the optically pure, diastereomeric salt resulting from step (f), (−)-β-[(2-amino-1-naphthalenyl)thio]-α-hydroxy-4-methoxybenzenepropanoic acid (−)-1-(p-hydroxybenzyl)-1,2,3,4,5,6,7,8-octanhydroisoquanoline hydrate, with an inorganic acid.

DETAILED DESCRIPTION OF THE INVENTION

The invention relates to a process for preparing optically active naphtho[1,2-b][1,4]thiazepin-4(5H)-ones. The process involves resolution of the racemic acid, rac-β-[(2-amino-1-naphthalenyl)thio]-α-hydroxy-4-methoxybenzenepropanoic acid of the formula

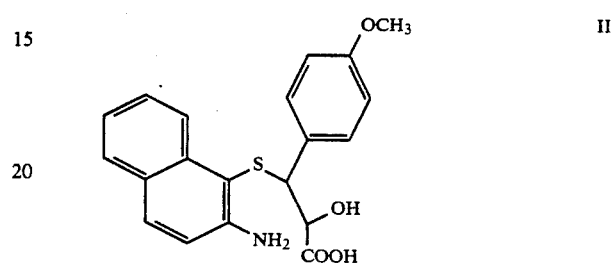

into its enantiomers (+)-β-([2-amino-1-naphthalenyl)thio]-α-hydroxy-4-methoxybenzenepropanoic acid and (−)-β-([2-amino-1-naphthalenyl)thio]-α-hydroxy-4-methoxybenzenepropanoic acid of the formulas

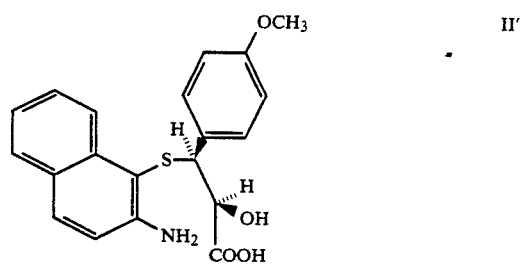

and

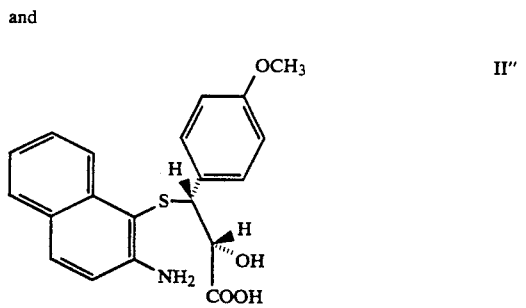

The process specifically comprises:

(a) treatment of a solution of the racemic acid rac-β-[(2-amino-1-naphthalenyl)thio]-α-hydroxy-4-methoxybenzenepropanoic acid with (+)-1-(p-hydroxybenzyl)-1,2,3,4,5,6,7,8-octahydroisoquinoline to form diastereomeric salts (+)-β-([2-amino-1-naphthalenyl) thio]-α-hydroxy-4-methoxybenzenepropanoic acid (+)-1-(p-hydroxybenzyl)-1,2,3,4,5,6,7,8-octahydroisoquinoline hydrate which crystallizes and (−)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate, which remains in solution;

(b) separating the crystalline diastereomeric salt of step (a) by filtration and purifying by recrystallization;

(c) obtaining the enantiomeric acid (+)-β-[(2-amino-1-naphthalenyl)thio]-α-hydroxy-4-methoxybenzenepropanoic acid by the treatment of its corresponding optically active salt with an inorganic acid; and (d) recovering the resolving agent (+)-1-(p-hydroxybenzyl)-1,2,3,4,5,6,7,8-octahydroisoquinoline.

(e) concentrating the mother liquor from step (b) and isolating crude (−)-β-[(2-amino-1-naphthalenyl)thio]-α-hydroxy-4-methoxybenzenepropanoic acid by extraction;

(f) treating the crude (−)-β-[(2-amino-1-naphthalenyl)thio]-α-hydroxy-4-methoxybenzenepropanoic acid isolated from step (e) with (−)-1-(p-hydroxybenzyl)-1,2,3,4,5,6,7,8-octahydroisoquinoline; and (g) obtaining the enantiomeric acid (−)-β-[(2-amino-1-naphthalenyl)thio]-α-hydroxy-4-methoxybenzenepropanoic acid by treating the salt resulting from step (f) (−)-β-[(2-amino-1-naphthalenyl) thio]-α-hydroxy-4-methoxybenzenepropanoic acid (−)-1-(p-hydroxybenzyl)-1,2,3,4,5,6,7,8-octahydroisoquinoline hydrate with inorganic acid.

The resolutions of the compound of formula II

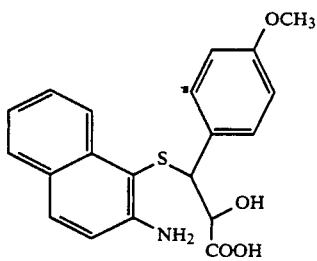

which is a rac-β-[(2-amino-1-naphthalenyl)thio]-α-hydroxy-4-methoxybenzenepropanoic acid into compounds of formulas

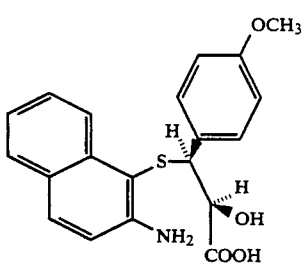

and

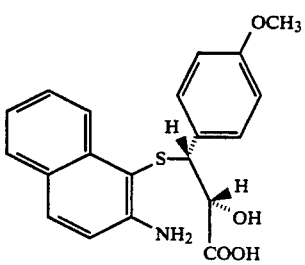

can be carried out with the resolving agent of formula III

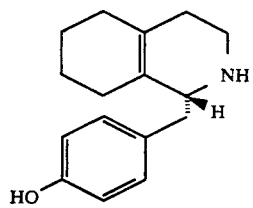

which is (+)-1-(p-hydroxybenzyl)-1,2,3,4,5,6,7,8-octahydroisoquinoline by dissolving the two just mentioned compounds of formula II and formula III in absolute ethanol heated on a steam bath. The resulting solution may optically be treated with seed crystals of the salt mentioned just below. The resulting salt (+)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate crystallizes and can be separated by filtration and purified by recrystallization. The compound of formula II is disclosed in U.S. Pat. No. 4,652,561.

The just above mentioned salt can be decomposed by treatment with an inorganic acid such as sulfuric acid or more preferably hydrochloric acid to obtain optically pure enantiomeric acid (+)-β-[(2-amino-1-naphthalenyl)thio]-α-hydroxy-4-methoxybenzenepropanoic acid of formula II'

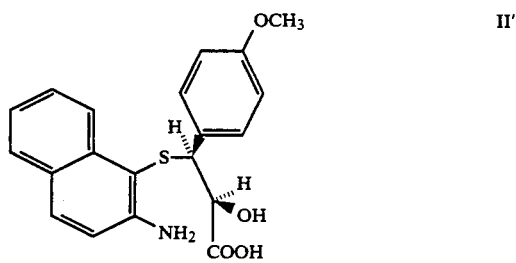

The resolving agent, (+)-1-(p-hydroxybenzyl)-1,2,3,4,5,6,7,8-octahydroisoquinoline is known as set forth in Helvetic Chimica Acta, Volume 39, fasciculus II (1956) Number 49—49 pages 429–440 which is incorporated herein by reference.

U.S. Pat. No. 4,652,561 is also incorporated herein be reference.

The resolving agent, (+)-1-(p-hydroxybenzyl)-1,2,3,4,5,6,7,8-octahydroisoquinoline may be recovered by making basic the above described solution which was treated with inorganic acid. The base used may be ammonium hydroxide. The resulting suspension is extracted with an organic solvent such as chloroform or more preferably methylene chloride, and the above mentioned resolving agent is recovered by usual separatory techniques.

The compound of formula II"

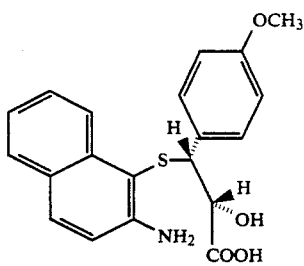

II"

which is (−)-β-[(2-amino-1-naphthalenyl)thio]-α-hydroxy-4-methoxybenzenepropanoic acid can be obtained by combining the mother liquors obtained in the separation of the above mentioned diastereomeric salt (+)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate. These combined mother liquors are concentrated to dryness, the residue is decomposed with an inorganic acid such as sulfuric acid, or more preferably hydrochloric acid. The resulting suspension is extracted with an organic solvent such as methylene chloride or more preferably ethyl acetate.

Removal of this organic solvent gives crude (−)-β-[(2-amino-1-naphthalenyl)thio]-α-hydroxy-4-methoxybenzenepropanoic acid which is further purified by reaction with the resolving agent (−)-1-(p-hydroxybenzyl)-1,2,3,4,5,6,7,8-octahydroisoquinoline in absolute ethanol heated on a steam bath. The resulting solution may optionally be seeded with a few crystals of the salt mentioned just below. The resulting diastereomeric salt (−)-β-[(2-amino-1-naphthalenyl)thio]-α-hydroxy-4-methoxybenzenepropanoic acid (−)-1-(p-hydroxybenzyl)-1,2,3,4,5,6,7,8-octahydroisoquinoline is separated by filtration and further purified by recrystallization.

In this manner, the just above mentioned salt may be obtained in substantially optically pure form. Succeeding compounds in the synthesis may also be obtained in substantially optically pure form by the process disclosed herein.

Recovery of (−)-β-[(2-amino-1-naphthalenyl)thio]-α-hydroxy-4-methoxybenzenepropanoic acid of formula II"

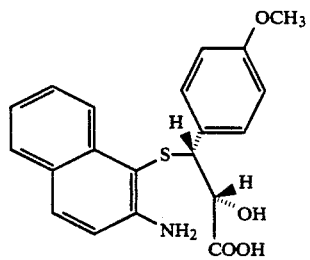

II"

is achieved by decomposing the just above mentioned diastereomeric salt with an inorganic acid such as sulfuric acid, or more preferably hydrochloric acid. The resulting suspension is extracted with an organic solvent such as methylene chloride or more preferably ethyl acetate. The just above mentioned acid is then recovered by usual separatory techniques.

Recovery of (−)-1-(p-hydroxybenzyl)-1,2,3,4,5,6,7,8-octahydroisoquinoline can be achieved by making basic the solution which was acidified to obtain the (−)-β-[(2-amino-1-naphthalenyl)thio]-α-hydroxy-4-methoxybenzenepropanoic acid. The base used is ammonium hydroxide. The resulting suspension is extracted with an organic solvent such as chloroform or more preferably methylene chloride. The (+)-1-(p-hydroxybenzyl)-1,2,3,4,5,6,7,8-octahydroisoquinoline may be obtained from the extracts by usual separatory techniques.

The optically pure β-[(2-amino-1-naphthalenyl)thio]-α-hydroxy-4-methoxybenzenepropanoic acids obtained may be used to prepare optically pure naphtho[1,2-b][1,4]thiazepin-4(5H)-ones. Naphtho[1,2-b][1,4]thiazepin-4(5H)-ones have activity as calcium channel blockers and accordingly, are useful as agents for lowering blood pressure, and as agents for treating ischemia.

The optically pure just above mentioned acids may be converted to the end product naphtho[1,2-b][1,4]thiazepin-4(5H)-ones as follows.

A compounds of formula II' or II" can be cyclized respectively to the compounds of formula

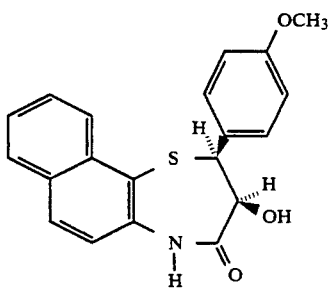

IV' or

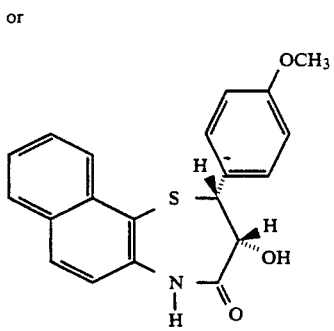

IV"

by reaction in the presence of a catalytic amount of an acid such as p-toluenesulfonic acid in an aromatic solvent such as, benzene, xylene or more preferably toluene, at reflux for a period of about 12 to about 72 hours. Isolation of compounds of formula IV' or IV" can be by conventional means such as recrystallization.

It will be understood that formula

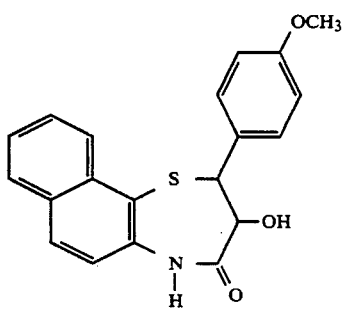

IV encompasses compounds of formulas IV' and IV"

A compound of formula IV can be converted to a compound of formula

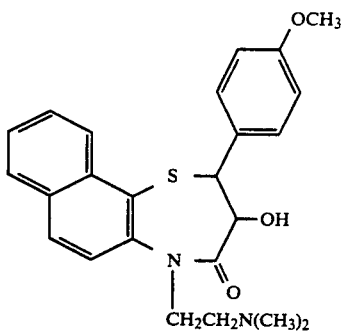

by reaction with the compound of the formula

The reaction is carried out by reacting an alkali metal salt of a compound of formula IV, such as the sodium or more preferably potassium salt thereof with an aminoalkyl halide of formula V, preferably the chloride thereof, in a polar organic solvent such as, methyl acetate, or more preferably ethyl acetate, at about 40° to about 80°, or at the reflux temperature of the solvent employed, which in the case of ethyl acetate is 77°, for a period of about 1 hour to about 17 hours. The reaction is carried out in the presence of a base, such as, potassium hydroxide in acetone or more preferably potassium carbonate in acetone or in a lower alkyl acetate. Separation of the compound of formula Ia can be by conventional means such as crystallization.

Specifically, a compound of formula Ia, can be acylated by reaction with acetic anhydride, or acetyl chloride optionally in the presence of a base such as, pyridine, triethylamine, or dimethylaniline at room temperature or up to about 115°.

Alternatively, an alkali metal salt, such as a sodium salt, of a compound of formula Ia may be reacted with an alkylating agent such as dialkyl sulfate, more particularly, dimethyl sulfate in an aromatic solvent such as toluene or more preferably benzene, at about reflux temperature for about 10 minutes to about 2 hours.

Also, a compound of formula Ia may be reacted with an alkyl halo formate such as ethyl chloroformate in a basic solvent such as pyridine at about ice bath temperatures.

Moreover, a compound of formula Ia may be reacted with an alkoxy alkanoyl halide such as, methoxyacetyl chloride in a basic solvent such as pyridine at about ice bath temperatures.

Furthermore, a compound of formula Ia may be reacted with a cycloalkylcarboxylic acid halide, such as, cyclopropane carboxylic acid chloride in a basic solvent such as pyridine at about ice bath temperatures.

All of the just above mentioned reactions of compounds of formula Ia yield compounds of formula Ib

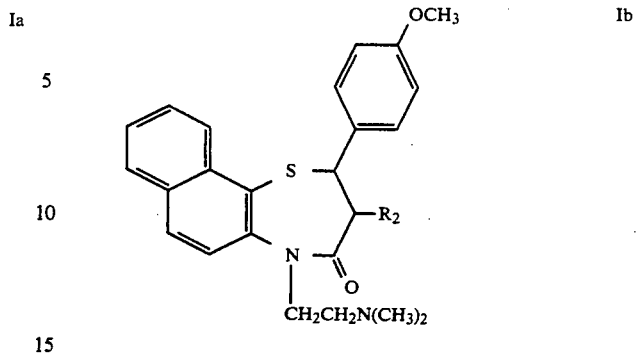

wherein $R_2$ is lower alkanoyloxy, lower cyclocarbonyloxy;

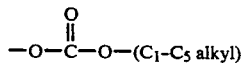

or

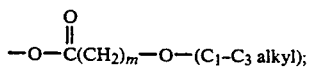

wherein m is 1 to 2.

Compounds of formulas Ia and Ib are encompassed by formula I

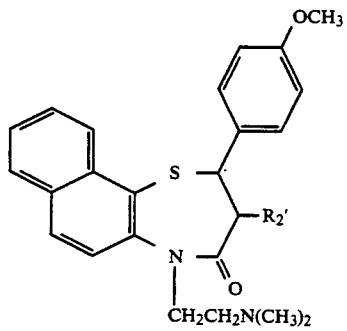

wherein $R_2$ is hydroxy, lower alkanoyloxy, lower cyclocarbonyloxy;

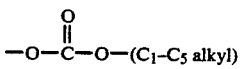

or

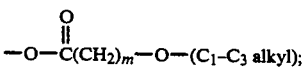

wherein m is 1 to 2.

Processes for converting a compound of formula Ia to a compound of formula I are set forth in more detail in U.S. Pat. No. 4,652,561.

Compounds of formula I, as described in U.S. Pat. No. 4,652,561, are calcium channel blockers useful as agents for lowering blood pressure and treating ischemia.

It can be seen that the difference between the process of the invention and the process set forth in U.S. Pat. No. 4,652,561, is that in the process of the invention, the resolution into optically active enantiomers occurs at an early stage giving compounds of the formulas

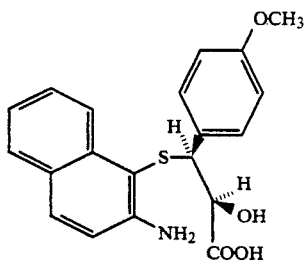

and

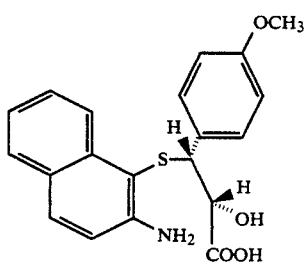

whereas in U.S. Pat. No. 4,652,561 separation at a late stage yields, optically active enantiomers of the formulas

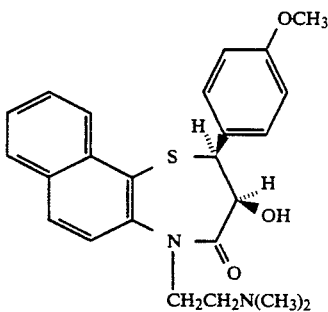

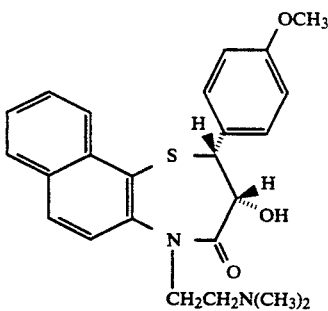

An advantage to the present process is that resolution into optically active enantiomers at the earlier stage as the just above mentioned acids of formulas II' and II''' means that the process can be carried out using smaller amounts of reactants with a resulting saving in expense.

A further advantage of the process of the invention is the recovery of resolving agent. Recovering of the resolving agent is economical and further avoids pollution of the environment with by-products of the process.

The examples which follow, further illustrate the invention. All temperatures are in degrees Celsius unless otherwise mentioned.

EXAMPLE 1

Resolution of rac-β-[(2-Amino-1-naphthalenyl)thio]-α-hydroxy-4-methoxybenzenepropanoic Acid A mixture of 7.38 g (0.0199 mol) of (±)-β-[(2-amino-1-naphthalenyl)thio]-α-hydroxy-4-methoxybenzenepropanoic acid and 4.84 g (0.0199 mol) of (+)-1-(p-hydroxybenzyl)-1,2,3,4,5,6,7,8-octahydroisoquinoline in 400 mL of ethanol (absolute) was heated on the steam bath until clear solution obtained, then seeded with a few crystals of (+)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate and allowed to crystallize at room temperature overnight. The crystals were separated by filtration and dried to yield 6.3 g of salt, mp 145°–147° (decomposes, shrinks at 140°), $[\alpha]_D^{25} +290°$ (C 0.5, MeOH-heat the sample to dissolve). One recrystallization from methanol (390 mL) as above yielded 5.75 g (91.2%) of pure (+)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate, mp 142°–144° (decomposes, shrinks at 140°), $[\alpha]_D^{25} +288.71°$ (C 0.195, MeOH).

$C_{20}H_{19}NO_4S \cdot C_{16}H_{21}NO \cdot H_2O(630.80)$
Calcd: C, 68.55; H, 6.71; N, 4.44
Found: C, 68,90; H, 6.72; N, 4.38

EXAMPLE 2

(+)-β-[(2-Amino-1-naphthalenyl)thio]-α-hydroxy-4-methoxybenzenepropanoic Acid (30 )-β-[(2-Amino-1-naphthalenyl)thio]-α-hydroxy-4-methoxybenzenepropanoic acid (+)-1-(p-hydroxybenzyl-1,2,3,4,5,6,7,8-octahydroisoquinoline, 5.0 g (0.0079 mol) was decomposed in 60 mL 1N HCl. The resulting suspension was extracted with ethyl acetate (3×100 mL). The combined ethyl acetate solutions were dried (MgSO$_4$) and removal of the solvent gave 3.25 g of crude acid of the title. Recrystallization from CHCl$_3$ (10 mL) overnight afforded 2.81 g (96.2%) of (+)-β-[(2-amino-1-naphthalenyl)thio]-α-hydroxy-4-methoxybenzenepropanoic acid, mp 143°–145°. The analytical sample was recrystallized from benzene, mp 143°–145°, $[\alpha]_D^{25} +269.51°$ (C 0.52, MeOH).

$C_{20}H_{19}NO_4S(369.36)$
Calcd: C, 65.02; H, 5.18; N, 3.79
Found: C, 65.00; H, 5.20; N, 3.75

EXAMPLE 3

Recovery of (+)-1-(p-Hydroxybenzyl)-1,2,3,4,5,6,7,8-octahydroisoquinoline

The 1N HCl solution obtained in the isolation of (+)-acid in Example 2 was made basic with concentrated NH$_4$OH and the resulting suspension was extracted with methylene chloride (2×75 mL). The combined CH$_2$Cl$_2$ solutions were dried (MgSO$_4$) and removal of the solvent gave 1.5 g (78.1%) of (+)-1-(p-hydroxybenzyl)-1,2,3,4,5,6,7,8-octahydroisoquinoline, mp 156°–158° (no mixture mp depression with an authentic sample), $[\alpha]_D^{25} +165°$ (C 1.0, MeOH).

EXAMPLE 4

(−)-β-[(2-Amino-1-naphthalenyl)thio]-α-hydroxy-4-methoxybenzenepropanoic Acid

The combined mother liquors obtained in the separation of (+)-β-[(2-amino-1-naphthalenyl)thio]-α-hydroxy-4-methoxybenzenepropanoic acid (+)-1-(p-hydroxybenzyl)-1,2,3,4,5,6,7,8-octahydroisoquinoline hydrate were concentrated to dryness. The residue was decomposed with 75 mL of 1N HCl and the resulting suspension was extracted with ethyl acetate (3×100 mL). The combined ethyl acetate solutions were dried (MgSO$_4$) and removal of the solvent gave 3.91 g of crude (−)-β-[(2-amino-1-naphthalenyl)thio]-α-hydroxy-4-methoxybenzenepropanoic acid.

A mixture of 3.91 g (0.011 mol) of crude (−)-β-[(2-amino-1-naphthalenyl)thio]-α-hydroxy-4-methoxybenzenepropanoic acid, 2.57 g (0.011 mol) of (−)-1-(p-hydroxybenzyl)-1,2,3,4,5,6,7,8-octahydroisoquinoline in 110 mL of ethanol (absolute) was heated on the steam bath until a clear solution was obtained, then seeded with a few crystals of (−)-β-[(2-amino-1-naphthalenyl)thio-α-hydroxy-4-methoxybenzenepropanoic acid (−)-1-(p-hydroxybenzyl)-1,2,3,4,5,6,7,8-octahydroisoquinoline hydrate and allowed to crystallize at room temperature overnight. The crystals were separated by filtration and dried to yield 5.91 g of salt, mp 142°–144° (decomposition, shrinks at 140°). One recrystallization from ethanol (365 mL) overnight yielded 5.4 g (85.7%) of pure (−)-β-[(2-amino-1-naphthalenyl)thio]-α-hydroxy-4-methoxybenzenepropanoic acid (−)-1-(p-hydroxybenzyl)-1,2,3,4,5,6,7,8-octahydroisoquinoline hydrate, mp 145°–147° (decomposition, shrinks at 140°), $[\alpha]_D^{25} -285.74°$ (C 0.25, MeOH; heat the sample to dissolve).

C$_{20}$H$_{19}$NO$_4$S·C$_{16}$H$_{21}$NO·H$_2$O(630.80)
Calcd: C, 68.55; H, 6.71; N, 4.44
Found: C, 68.98; H, 6.46; N, 4.37

EXAMPLE 5

Recovery of (+)-1-(p-Hydroxybenzyl)-1,2,3,4,5,6,7,8-octahydroisoquinoline

The 1N HCl solution obtained in the isolation of (−)-β-[(2-amino-1-naphthalenyl)thio]-α-hydroxy-4methoxybenzenepropanoic acid was made basic with concentrated NH$_4$OH and the resulting suspension was extracted with methylene chloride (3×75 mL). The combined CH$_2$Cl$_2$ solutions were dried (MgSO$_4$) and removal of the solvent gave 2.36 g of (+)-1-(p-hydroxybenzyl)-1,2,3,4,5,6,7,8-octahydroisoquinoline, mp 154°–156° (no mixture mp depression with authentic sample), $[\alpha]_D^{25} +162°$ (C 1.0, MeOH).

EXAMPLE 6

(−)-β-[(2-Amino-1-naphthalenyl)thio]-α-hydroxy-4-methoxybenzenepropanoic Acid (−)-β-[(2-Amino-1-naphthalenyl)thio]-α-hydroxy-4-methoxybenzenepropanoic acid (−)-1-(p-hydroxybenzyl)-1,2,3,4,5,6,7,8-octahydroisoquinoline, 4.9 g (0.0077 mol) was decomposed in 60 mL of 1N HCl. The resulting suspension was extracted with ethyl acetate (3×100 mL). The combined ethyl acetate solutions were dried (MgSO$_4$) and removal of the solvent gave 2.9 g of crude (−)-β-[(2-amino-1-naphthalenyl)thio]-α-hydroxy-4-methoxybenzenepropanoic acid. Recrystallization rom CHCl$_3$ (10 mL) overnight afforded 2.37 g (82.8%) of (−)-β-[(2-amino-1-naphthalenyl) thio]-α-hydroxy-4-methoxybenzenepropanoic acid, mp 142°–144°. The analytical sample was recrystallized from benzene, mp 143°–145°, $[\alpha]_D^{25} -268.32°$ (C 0.476, MeOH).

C$_{20}$H$_{19}$NO$_4$S(369.36)
Calcd: C, 65.02; H, 5.18; N, 3.79
Found: C, 64.89; H, 5.20; N, 3.77

EXAMPLE 7

Recovery of (−)-1-(p-Hydroxybenzyl)-1,2,3,4,5,6,7,8-octahydroisoquinoline

The 1N HCl solution obtained in the isolation of (−)-β-[(2-amino-1-naphthalenyl)thio]-α-hydroxy-4-methoxybenzenepropanoic acid was made basic with concentrated NH$_4$OH and the resulting suspension was extracted with methylene chloride (2×100 mL). The combined CH$_2$Cl$_2$ solutions were dried (MgSO$_4$) and removal of the solvent gave 1.6 g (84.6%) of (−)-1-(p-hydroxybenzyl)-1,2,3,4,5,6,7,8-octahydroisoquinoline, mp 156°–158° (no mix mp depression with authentic sample), $[\alpha]_D^{25} -162°$ (C 1.0 MeOH).

EXAMPLE 8

[2S-(2β,3β)]-2,3-Dihydro-3-hydroxy-2-(4-methoxyphenyl)-naphtho[1,2-b][1,4]thiazepin-4(5H)-one A mixture of 1.0 g (0.0027 mol) of (+)-β-[(2-amino-1-naphthalenyl)thio]-α-hydroxy-4-methoxybenzenepropanoic acid and 0.1 g of p-toluensulfonic acid in 50 ml of xylene was stirred and heated at reflux for 1.5 hours using a Dean-Stark water trap. The reaction mixture wax cooled and the crystals were collected to afford 0.8 g (90%) of [2S-(2β,3β)]-2,3-dihydro-3-hydroxy-2-(4-methoxyphenyl) naphtho[1,2-b][1,4]thiazepin-4(5H)-one, mp 240°–241°, $[\alpha]_D^{25} +24.65°$ (C 0.495, acetone).

C$_{20}$H$_{17}$NO$_3$S(351.34)
Calcd: C, 68.37; H, 4.88; N, 3.99
Found: C, 68.42; H, 4.80; N, 3.92

EXAMPLE 9

(+)-cis-2,3-Dihydro-3-hydroxy-5-[2-(dimethylamino)ethyl]-2-(4-methoxyphenyl)naptho[1,2-b][1,4thiazepin-4(5H)-one A mixture of 0.5 g (0.0014 mol) of [2S-(2β,3β)]-2,3-dihydro-3-hydroxy-2-(4-methoxyphenyl)naphtho[1,2-b][1,4]-thiazepin-4(5H)-one, 0.23 g (0.0017 mol) of powdered potassium carbonate and 0.2 g (0.00158 mol) of 2-dimethylaminoethyl chloride in 30 ml of ethyl acetate was stirred and heated at reflux for 2 hours, then three times an additional 50 mg of 2-dimethylaminoethyl chloride was added at 2 hour intervals. The mixture was heated at reflux for a total of 12 hours, then cooled to room temperature, diluted with ethyl acetate and washed with brine. The ethyl acetate solution was dried (MgSO$_4$) and removal of the solvent gave 0.6 g of crude product, which on crystallization from ethyl acetate gave 0.5 g (85%) of (+)-cis-2,3-dihydro-3-hydroxy-5-[2-(dimethylamino)ethyl]-2-(4-methoxyphenyl)naphtho[1,2-b][1,4]thiazepin-4(5H)-one, mp 170°–172°, $[\alpha]_D^{25} +40.0°$ (C 1.0, MeOH).

EXAMPLE

[2R-(2α,3α)]-2,3-Dihydro-3-hydroxy-2-(4-methoxyphenyl)naphtho[1,2-b][1,4]thiazepin-4(5H)-one A mixture of 1.0 g (0.0027 mol) of (−)-β-[(2-amino-1-naphthalenyl)thio]-α-hydroxy-4-methoxybenzenepropanoic acid and 0.1 g of p-toluenesulfonic acid in 50 ml of xylene was stirred and heated at reflux for 1.5 hours using a Dean-Stark water strap. After cooling the crystals were collected to provide 0.80 g (80%) of [2R-(2α,3α)]-2,3- dihydro-3-hydroxy-2-(4-methoxyphenyl)-naphtho[1,2-b][1,4]thiazepin-4(5H)-one, mp 238°-239°, $[\alpha]_D^{25} -22.97°$ (C 0.51, acetone).

$C_{20}H_{17}NO_3S$ (351.34)

Calcd: C, 68.37; H, 4.88; N, 3.99

Found: C, 68.49; H, 4.68; H, 3.96

We claim:

1. (+)-β-[(2-amino-1-naphthalenyl)-thio]-α-hydroxy-4-methoxybenzenepropanoic acid (+)-1-(p-hydroxybenzyl)-1,2,3,4,5,6,7,8-octahydroisoquinoline hydrate.

2. (−)-β-[(2-amino-1-naphthalenyl)-thio-]α-hydroxy-4-methoxybenzenepropanoic acid (−)-1-(p-hydroxybenzyl)-1,2,3,4,5,6,7,8-octahydroisoquinoline hydrate.

* * * * *